United States Patent [19]

Reiter et al.

[11] Patent Number: 4,831,029

[45] Date of Patent: May 16, 1989

[54] CONDENSED CYCLIC TRIAZOLE DERIVATIVES, PHARMACEUTICAL COMPOSITIONS AND USE

[76] Inventors: József Reiter, 32/B Mihaályfi E. u. 1022; Endre Rivó, 1, Joliot Curie tér 1126; Klára Reiter née Esess, 32/B Mihályfi E. u. 1022; Márton Fekete, 49, Fö u. 1027; Frigyes Gögényi, 60a, Szakasits Á. u. 1115; Lujza Petö z, 2. Róczi tér 1089; István Gacsályi, 67, Baross u. 1201; István Gyertyán, 32, Borsó u. 1173, all of Budapest, Hungary

[21] Appl. No.: 116,870

[22] Filed: Nov. 5, 1987

[30] Foreign Application Priority Data

Nov. 5, 1986 [HU] Hungary ............................. 4602/86

[51] Int. Cl.$^4$ ................. A61K 31/505; A61K 31/535; C07D 471/14
[52] U.S. Cl. ................................. 514/232.5; 514/212; 514/233.2; 514/253; 514/254; 514/267; 540/481; 540/600; 544/81; 544/115; 544/251
[58] Field of Search ........................ 544/81, 115, 251; 514/183, 212, 232.5, 233.2, 253, 254, 267; 540/481, 600

[56] References Cited

U.S. PATENT DOCUMENTS 2,444,607 7/1948 Heimbach ........................... 544/251

Primary Examiner—Robert W. Ramsuer
Attorney, Agent, or Firm—Keil & Weinkauf

[57] ABSTRACT

The invention relates to condensed cyclic triazole derivatives of the general Formula I

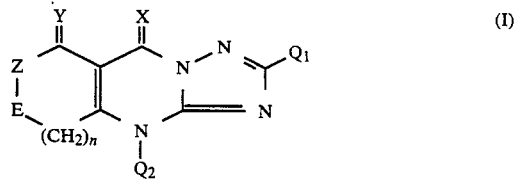

and pharmaceutically acceptable salts thereof.

The compounds of the general Formula I possess useful sedative and tranquillant properties and exhibit particularly spasmolytic, motility inhibiting, and narcosis potentiating, yohimbine potentiating and local anaesthetic and also weak reserpine ptosis inhibiting effect.

3 Claims, No Drawings

CONDENSED CYCLIC TRIAZOLE DERIVATIVES, PHARMACEUTICAL COMPOSITIONS AND USE

This invention relates to new condensed triazole derivatives, a process for the preparation thereof and pharmaceutical compositions containing the same.

According to an aspect of the present invention there are provided new cyclic triazolo derivatives of the general Formula I

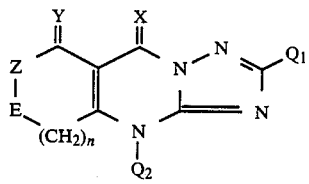

(wherein $Q_1$ is hydrogen, morpholino or a group of the general Formula $-NR_3R_4$ wherein $R_3$ and $R_4$ each stand for hydrogen or straight or branched chain, saturated or unsaturated lower alkyl, aralkyl or aryl, optionally substituted by one or more lower alkyl and/or halogen; or $R_3$ and $R_4$ together with the adjacent nitrogen atom, they are attached to, form a 5–8 membered heterocyclic ring; or a group of the general Formula

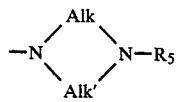

wherein

Alk and Alk' each stand for lower alkylene chain and $R_5$ represents lower alkyl or aralkyl; or a group of the general Formula
$-SR_6$ wherein $R_6$ stands for lower alkyl or aralkyl being unsubstituted or substituted by one or more halogen atom(s);

$Q_2$ stands for hydrogen, lower alkyl, aralkyl or a group of the general Formula

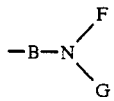

wherein

B is lower alkylene;

F and G each stand for lower alkyl or aralkyl or together with the adjacent nitrogen atom, they are attached to, form a 5–8 membered heterocyclic ring;

n is 0 or 1;

X and Y stand for =O or =H$_2$, with the proviso that X and Y are different;

E and Z stand for $-CH_2-$, $-NH-$, $-N$-alkyl-, $-N$-aralkyl-, or $NCOR_1$ wherein $R_1$ is lower alkyl or aralkyl; or

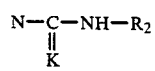

wherein

K is =O or =S and $R_2$ stands for straight or branched chain alkyl, aralkyl, or aryl which can be either unsubstituted or can bear one or more alkyl and/or haloalkyl substituent(s);

with the proviso that Z and E are different and one of Z and E represents $-CH_2-$) and mixtures and pharmaceutically acceptable salts thereof.

The compounds of the general Formula I can appear in various mesomeric, tautomeric and stereoisomeric forms. The invention encompasses all mesomeric, tautomeric and stereoisomeric forms of the compounds of the general Formula I and mixtures thereof.

The compounds of the general Formula I possess low toxicity and exhibit useful sedative-tranquillant effects and exert particularly valuable spasmolytic, motility inhibiting, yohimbine potentiating, local ahaesthetic and narcosis potentiating activity and also a weak reserpine ptosis inhibitory effect.

The results of the pharmacological tests showing the activity of the compounds of the general Formula I are summarized in Table I.

TABLE I

Pharmacological activity of compounds of the general Formula I

| Test compound Example No. | Spasmolytic effect | Hexobarbital narcosis potentiating effect | Motility inhibiting effect | Yohimbin potentiating effect | Local anaesthetic effect |
|---|---|---|---|---|---|
| 18 | ED$_{50}$ 150 mg/kg T.I. = 6.6 | | | | |
| 19 | | ED$_{50}$ 200 mg/kg T.I. = 6.0 | ED$_{50}$ 200 mg/kg T.I. = 6.0 | | |
| 20 | ED$_{50}$ 155 mg/kg T.I. = 6.5 | | | | |
| 19c | ED$_{50}$ 150 mg/kg T.I. = 6.7 | | | T.I. = 47 | |
| 19g | ED$_{50}$ 100 mg/kg T.I. = 8.5 | | | | EC$_{50}$ 0.16 potentiating ratio |
| Meprobamat | | ED$_{50}$ 260 mg/kg T.I. = 4.1 | ED$_{50}$ 270 mg/kg T.I. = 4.1 | | |
| Trimetadion | ED$_{50}$ 490 mg/kg T.I. = 4.3 | | | | |
| Amitriptilin | | | | ED$_{50}$ 12.5 mg/kg | |
| Lidocain | | | | | EC$_{50}$ 0.16 |

T.I. = therapeutical index

The LD$_{50}$ value of the test compounds is about 1000 mg/kg.

The following test methods are used: Motility inhibition test: J. Borsy, E. Csányi, J. Lázár: J. Arch. Int. Pharmacodyn. 124, 1-2 (1960); Inhibition of tetracor spasms: R. Benzinger, D. Hane: Arch. Int Pharmacodyn. 167, 245-249 (1967).

The yohimbine potentiating effect is determined by the method of R. M. Quinton: Brit. J. Pharmacol. 21, 51-66 (1963) and the local anaesthetic effect is tested according to the method of A. P. Trusnt and D. D'Amato: Acta Chir. Scand. 116, 351 (1958).

In the hexobarbital narcosis potentiating test those animals are regarded as showing positive reaction in which the average narcosis time is lengthened to at least 2.5-fold of that of the control group.

The ED$_{50}$ values are calculated from the data thus transformed.

According to a further aspect of the present invention there is provided a process for the preparation of compounds of the general Formula I (wherein $Q_1$, $Q_2$, X, Y, Z, E and n are as stated above) and mixtures and pharmaceutically acceptable salts thereof, which comprises (a) for the preparation of compounds of the general Formula I, wherein $Q_2$ stands for hydrogen and the other symbols are as stated above, reacting a compound of the general Formula II

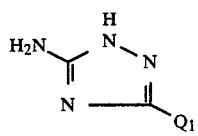 (II)

(wherein $Q_1$ is as stated above) with a compound of the general Formula III

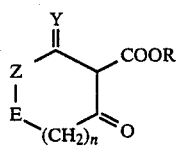 (III)

(wherein Z, E, Y and n are as stated above and R stands for lower alkyl) or (b) for the preparation of compounds of the general Formula I, wherein Z or E stands for a group

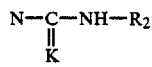

and the other symbols are as stated above, reacting a compound of the general Formula I, wherein Z or E stands for —NH—, with a compound of the general Formula VI $R^2$—N═C═K (VI)

(wherein $R^2$ and K are as stated above); or (c) for the preparation of compounds of the general Formula I, wherein Z or E stands for a group N—CO—$R_1$ and the other symbols are as stated above, reacting a compound of the general Formula I, wherein Z or E is —NH—, with a compound of the general Formula V $R^1$—COHal (V)

(wherein $R_1$ is as stated above and Hal is halogen) in the presence of an acid binding agent; or (d) for the preparation of compounds of the general Formula I, wherein $Q_2$ is other than hydrogen, reacting a compound of the general Formula I, wherein $Q_2$ stands for hydrogen, with a compound of the general Formula IV $Q_2'$-Hal (IV)

(wherein $Q_2'$ has the meaning of $Q_2$ except hydrogen and Hal is halogen); and, if desired, converting a compound of the general Formula I into a pharmaceutically acceptable salt thereof.

According to method (a) compounds of the general Formula I, wherein $Q_2$ stands for hydrogen, are prepared by reacting a compound of the general Formula II with a compound of the general Formula III. The reaction is preferably carried out by heating a mixture of the starting materials of the general Formulae II and III in a polar solvent (preferably n-butanol or acetic acid). The reaction is advantageously carried out at the boiling point of the solvent. The reaction time depends on the temperature and is generally 1–20 hours, preferably 3–8 hours. The compound of the general Formula I thus obtained is isolated from the reaction mixture by methods known per se (e.g. by crystallization or precipitation). Some compounds precipitate from the reaction mixture and can be isolated by filtration. If the product is not precipitated from the reaction mixture after heating the same to boiling, it can be separated by adding an excess of ammonium hydroxide, separating the crystalline product by filtration, dissolving the said product in an aprotic solvent (preferably dimethyl formamide) and precipitating the said product by adding a solvent having a different polarity from and being miscible with the first solvent (preferably acetonitrile).

According to method (b) compounds of the general Formula I, wherein Z or E stands for a group of the Formula

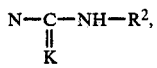

are prepared by reacting a compound of the general Formula I, wherein Z or E stands for —NH—, with a compound of the general Formula VI. The reaction is accomplished in an aprotic solvent (preferably dimethyl formamide or hexamethyl phosphoric triamide or a mixture thereof). The reaction is preferably carried out at a temperature between 30° C. and 150° C., particularly at about 140° C. The reaction time lies between 6 and 20 hours. The product is isolated by methods known per se (e.g. by precipitation).

According to method (c) compounds of the general Formula I, wherein Z or E stands for a group of the general Formula N—CO—$R_1$, are prepared by reacting a compound of the general Formula I, wherein Z or E stands for —NH—, with a compound of the general Formula V in the presence of an acid binding agent. The reaction may be carried out in an aprotic solvent (preferably dimethyl formamide or hexamethyl phosphoric triamide or a mixture thereof). As acid binding agent preferably triethyl amine can be used. The reaction may be accomplished at a temperature between 25°

C. and 65° C., particularly at 40°–50° C. The reaction time may vary between 2 and 7 hours, preferably 3–5 hours. The product may be isolated by methods known per se (e.g. by precipitation).

According to method (d) compounds of the general Formula I, wherein $Q_2$ is other than hydrogen, are prepared by reacting a compound of the general Formula I, wherein $Q_2$ stands for hydrogen, with a compound of the general Formula IV. The reaction may be preferably carried out in an aprotic solvent (preferably dimethyl formamide, xylene or a mixture thereof). One may proceed preferably by first converting the compound of the general Formula I, wherein $Q_2$ is hydrogen, into an alkali salt (preferably sodium salt) by treatment with an alkali hydride (preferably sodium hydride). To the alkali salt thus obtained a compound of the general Formula IV or a solution thereof formed with an aprotic solvent (advantageously xylene) is added and the reaction is accomplished at a temperature between 0° C. and 90° C., particularly at about 40° C. The reaction time may vary between about half an hour and 20 hours, and is preferably about 8 hours. The compound of the general Formula I thus obtained, wherein $Q_2$ is other than hydrogen, i.e. it is identical with the introduced $Q_2'$ group, can be isolated by known methods (e.g. by extraction).

The compound of the general Formula I thus obtained can be converted into pharmaceutically acceptable salts by methods known per se.

The starting materials of the general Formula II are known compounds or can be prepared by simple methods known per se [see e.g. J. Heterocyclic Chem. 19, 1157 (1982) and J. Heterocyclic Chem. 22, 385 (1985)].

The starting materials of the general Formula III are also known or can be prepared by simple methods known per se [see e.g. J. Am. Chem. Soc. 55, 1233 (1933); J. Org. Chem. 6, 507 (1969); J. Am. Chem. Soc. 65, 2458 (1943)].

The starting materials of the general Formula IV are well-known alkyl halides or dialkylamino-alkylhalides.

The starting materials of the general Formula V are well-known acyl halides.

The starting materials of the general Formula VI are well-known isocyanates or isothiocyanates.

According to a still further aspect of the present invention there are provided pharmaceutical compositions comprising as active ingredients at least one compound of the general Formula I or a pharmaceutically acceptable salt thereof in admixture with suitable inert solid or liquid carriers.

The pharmaceutical compositions of the present invention can be prepared by methods of pharmaceutical industry known per se.

The pharmaceutical compositions can contain conventional pharmaceutical carriers (e.g. starch, magnesium carbonate, magnesium stearate, talc, calcium carbonate, water etc.) and usual auxiliary agents (e.g. wetting, dispersing, emulsifying agents, buffers, salts for adjusting the osmotic pressure etc.). The active ingredient can be finished in solid (e.g. tablet, pill, coated pill, dragée, capsule), semi-solid (e.g. suppository) or liquid (e.g. solution, emulsion or suspension) form. The pharmaceutical compositions of the present invention are suitable for oral, parenteral or rectal administration.

The daily dose of the compounds of the general Formula I can vary between wide ranges and depends on various factors (e.g. activity of the active ingredient; art of administration; state and age of the patient etc.). The average daily oral dose is about 0.1–1000 mg/kg, preferably 25–3000 mg/kg, in 1–3 portions. The above values are but of informative character and the actual dose may also be above or below the above limits. The compositions used may be preferably tablets containing 50, 100 or 300 mg of the active ingredient.

Further details of the present invention are to be found in the following Examples without limiting the scope of protection.

EXAMPLE 1

2-Morpholino-6,7,8,9-tetrahydro-pyrido[4,3-d]-1,2,4-triazolo[1,5-a]pyrimidine-5(10H)-one and
2-morpholino-6,7,8,9-tetrahydro-pyrido[4,3-d]-1,2,4-triazolo[1,5-a]pyrimidine-6(10H)-one A mixture of 16.92 g (0.1 mole) of 5-amino-3-morpholino-1H-1,2,4-triazole, 20.77 g (0.1 mole) of 3-carbethoxy-4-piperidone-hydrochloride and 50 ml of acetic acid is heated to boiling for 13 hours. The precipitated crystals are filtered, washed with 20 ml of acetic acid and 200 ml of chloroform. To the 23.5 g (0.075 mole) of 2-morpholino-6,7,8,9-tetrahydro-pyrido[4,3-d]-1,2,4-triazolo[1,5-a]pyrimidine-5(10H)-one-hydrochloride thus obtained a solution of 3.00 g (0.075 mole) of sodium hydroxide in 250 ml of hot methanol is added, the mixture is heated to boiling for 10 minutes, filtered and washed with water and acetone. Thus 21.00 g of 2-morpholino-6,7,8,9-tetrahydro-pyrido[4,3-d]-1,2,4-triazolo[1,5-a]pyrimidine-5(10H)-one are obtained, yield 76%, m.p.: 308°–310° C.

The acetic acid/chloroform filtrate of the original reaction mixture is evaporated to dryness in vacuo. To the residue 100 ml of ethanol are added, whereupon the mixture is again evaporated to dryness in vacuo. To the oily residue 40 ml of 25% ammonium hydroxide are added. The precipitated crystals are filtered, washed with water and acetone and dried. The product is dissolved in hot hexamethyl phosphoric triamide and precipitated by adding acetonitrile. Thus 1.94 g of 2-morpholino-6,7,8,9-tetrahydro-pyrido[4,3-d]-1,2,4-triazolo[1,5-a]pyrimidine-6-(10H)-one are obtained, yield 8%, m.p.: above 350° C.

EXAMPLE 2

2-Methylthio-6,7,8,9-tetrahydro-pyrido[4,3-d]-1,2,4-triazolo[1,5-a]pyrimidine-5(10H)-one and
2-methylthio-6,7,8,9-tetrahydro-pyrido[4,3-d]-1,2,4-triazolo[1,5-a]pyrimidine-6(10H)-one A mixture of 13.02 g (0.1 mole) of 5-amino-3-methylthio-1H-1,2,4-triazole, 20.77 g (0.1 mole) of 3-carbethoxy-4-piperidone-hydrochloride and 50 ml of acetic acid is heated to boiling for 8 hours. The precipitated crystals are filtered, washed with 20 ml of acetic acid and 200 ml of chloroform. Thus 20.06 g of 2-methylthio-6,7,8,9-tetrahydropyrido[4,3-d]-1,2,4-triazolo-1,5-a]pyrimidine-5(10H)-one-hydrochloride are obtained. This product is dissolved in 500 ml of hot water, then 50 ml of a 10% sodium hydrogen carbonate solution are added. The mixture is cooled to room temperature, the precipitated crystals are filtered, washed with water and acetone, heated to boiling in 100 ml of hexamethyl phosphoric triamide for 15 minutes, and cooled to room temperature. The precipitate is filtered, washed with water and acetone. Thus 13.7 g of 2-methylthio-6,7,8,9-tetrahydro-pyrido[4,3-d]-1,2,4-triazolo-[1,5-a]pyrimidine-5(10H)-one are obtained, yield 58%, m.p.: 266°–269° C.

The acetic acid/chloroform filtrate of the original reaction mixture is evaporated to about 10-15 ml and to this residue 60 ml of a 25% ammonium hydroxide solution are added. The precipitated crystals are filtered, washed with water and acetone. The product is dissolved in 35 ml of hot hexamethyl phosphoric triamide and precipitated by adding 90 ml of acetonitrile. The precipitated crystals are filtered, washed with water and acetone. Thus 1.70 g of 2-methylthio-6,7,8,9-tetrahydro-pyrido[4,3-d]-1,2,4-triazolo[1,5-a]pyrimidine-6(10H)-one are obtained, yield 7%, m.p.: 314°-317° C.

EXAMPLE 3

7-Benzyl-2-morpholino-6,7,8,9-tetrahydro-pyrido[4,3-d]-1,2,4-triazolo[1,5-a]pyrimidine-5(10H)-one and 7-benzyl-2-morpholino-6,7,8,9-tetrahydro-pyrido[4,3-d]-1,2,4-triazolo[1,5-a]pyrimidine-6(10H)-one A mixture of 50.76 g (0.3 mole) of 5-amino-3-morpholino-1H-1,2,4-triazole, 85.13 g (0.3 mole) of 1-benzyl-3-carbomethoxy-4-piperidone-hydrochloride and 175 ml of acetic acid is heated to boiling for 6 hours. After cooling 400 ml of concentrated ammonium hydroxide solution are added to the reaction mixture, which is then allowed to stand at room temperature for 16 hours. The precipitated crystals are filtered and washed with 200 ml of water. The product is heated to boiling in 500 ml of methanol for 15 minutes, filtered, washed with 400 ml of methanol, dissolved in hot dimethyl formamide, precipitated by adding acetonitrile, filtered and washed with acetonitrile. Thus 78.81 g of 7-benzyl-2-morpholino-6,7,8,9-tetrahydro-pyrido[4,3-d]-1,2,4-triazolo[1,5-a]pyrimidine-5(10H)-one are obtained, yield 72%, m.p.: 291°-293° C. The crystals precipitated from the methanol solution are filtered, washed with methanol, dissolved in 60 ml of hot dimethyl formamide, precipitated by adding 60 ml of acetonitrile, filtered and washed with acetonitrile. Thus 6.63 g of 7-benzyl-2-morpholino-6,7,8,9-tetrahydro-pyrido[4,3-d]-1,2,4-triazolo[1,5-a]pyrimidine-6(10H)-one are obtained, yield 6%, m.p.: 252°-254° C.

EXAMPLE 4

7-Benzyl-2-dimethylamino-6,7,8,9-tetrahydro-pyrido[4,3-d]-1,2,4-triazolo[1,5-a]pyrimidine-5(10H)-one A mixture of 5.09 g (0.04 mole) of 5-amino-3-dimethylamino-1H-1,2,4-triazole, 11.35 g (0.04 mole) of 1-benzyl-3-carbomethoxy-4-piperidone-hydrochloride and 40 ml of acetic acid is heated to boiling for 2 hours. The reaction mixture is allowed to stand at room temperature for 16 hours. To the mixture 70 ml of a 25% ammonium hydroxide solution are added, the precipitated crystals are filtered and washed with hot methanol. The product is heated to boiling with 20 ml of methanol for 10 minutes and filtered again. The crystals are dried and dissolved in hot dimethyl formamide. The product is precipitated by adding acetonitrile, filtered and washed with acetone. Thus 12.179 g of 7-benzyl-2-dimethylamino-6,7,8,9-tetrahydro-pyrido[4,3-d]-1,2,4-triazolo[1,5-a]pyrimidine-5(10H)-one are obtained, yield 58%, m.p.: 279°-281° C.

In an analogous manner to the above Examples the following compounds of the general Formula I are prepared.

EXAMPLE 5

7-Benzyl-2-tert.butylamino-6,7,8,9-tetrahydro-pyrido[4,3-d]-1,2,4-triazolo[1,5-a]pyrimidine-5(10H)-one, m.p.: 257°-259° C., yield 63%.

EXAMPLE 6

7-Benzyl-2-piperidino-6,7,8,9-tetrahydro-pyridino[4,3-d]-1,2,4-triazolo[1,5-a]pyrimidine-5(10H)-one, m.p.: 245°-247° C., yield 69%.

EXAMPLE 7

7-Benzyl-2-diethylamino-6,7,8,9-tetrahydro-pyrido[4,3-d]-1,2,4-triazolo[1,5-a]pyrimidine-5(10H)-one, m.p.: 249°-252° C., yield 47%.

EXAMPLE 8

7-Benzyl-2-(2-methyl-phenyl-amino)-6,7,8,9-tetrahydro-pyrido[4,3-d]-1,2,4-triazolo[1,5-a]pyrimidine-6(10H)-one One proceeds according to Example 4, except that 5-amino-3-dimethylamino-1H-1,2,4-triazole is replaced by 7.57 g (0.04 mole) of 5-amino-3-(2-methyl-phenyl-amino)-1H-1,2,4-triazole and the reaction mixture is heated to boiling for 8 hours, instead of 2 hours. Thus 11.28 g of the desired compound are obtained, yield 73%, m.p.: 248°-250° C.

In an analogous manner to the preceding Example the following compounds are prepared:

EXAMPLE 9

7-Benzyl-2-benzylamino-6,7,8,9-tetrahydro-pyrido[4,3-d]-1,2,4-triazolo[1,5-a]pyrimidine-6(10H)-one, m.p.: 224°-226° C., yield 69%.

EXAMPLE 10

7-Benzyl-2-(4-methyl-piperazinyl)-6,7,8,9-tetrahydro-pyrido[4,3-d]-1,2,4-triazolo[1,5a]pyrimidine-6(10H)-one, m.p.: 220°-223° C., yield 56%.

EXAMPLE 10a

7-Benzyl-2-(2-phenyl-ethylamino)-6,7,8,9-tetrahydro-pyrido[4,3-d]-1,2,4-triazolo[1,5-a]pyrimidine-5(10H)-one, m.p.: 238°-242° C., yield 56%.

EXAMPLE 10b

7-Benzyl-2-diallylamino-6,7,8,9-tetrahydro-pyrido[4,3-d]-1,2,4-triazolo[1,5-a]pyrimidine-5(10H)-one, m.p.: 223°-226° C., yield 62%.

EXAMPLE 11

8-Benzyl-2-methylthio-6,7,8,9-tetrahydro-pyrido[3,4-d]-1,2,4-triazolo[1,5-a]pyrimidine-5(10H)-one A mixture of 39.05 g (0.3 mole) of 5-amino-3-methylthio-1H-1,2,4-triazole, 1-benzyl-4-carbethoxy-3-oxo-piperidine-hydrochloride and 110 ml of acetic acid is heated to boiling for 6.5 hours. The reaction mixture is allowed to stand overnight, the precipitate is filtered and washed with acetone. Thus 115.30 g of the crude product are obtained. The crude product is dissolved in 130 ml of hot pyridine, and to the pyridine solution 400 ml of acetone are added. The precipitated crystals are filtered, washed with acetone, the product is dissolved in 270 ml of pyridine and 1000 ml of acetone are added to the pyridine solution. The precipitated crystals are filtered and washed with acetone. Thus 89.3 g of the desired compound are obtained, yield 91%, m.p.: 232°–234° C.

EXAMPLE 12

8-Benzyl-2-morpholino-6,7,8,9-tetrahydro-pyrido[3,4-d]-1,2,4-triazolo[1,5-a]pyrimidine-5(10H)-one A mixture of 50.8 g (0.3 mole) of 5-amino-3-morpholino-1H-1,2,4-triazole, 89.3 g (0.3 mole) of 1-benzyl-4-carbethoxy-3-oxo-piperidine-hydrochloride and 220 ml of acetic acid is refluxed for 7 hours under stirring. The reaction mixture is allowed to stand overnight, the precipitate is filtered and washed with acetone. The product thus obtained is dissolved in a mixture of 400 ml of water and 100 ml of pyridine under heating to boiling for 15 minutes. The solution is allowed to stand for a day, the precipitated crystals are filtered and washed with acetone. The product thus obtained (83.9 g) is dissolved in 260 ml of hot pyridine, to the solution 1000 ml of acetone are added. The precipitated crystals are filtered and washed with acetone. Thus 78.9 g of the desired compound are obtained, yield 72%, m.p.: 315°–317° C.

EXAMPLE 13

7-Phenyl-7,8-dihydro-6H-pyrrolo[3,4-d]-1,2,4-triazolo[1,5-a]pyrimidine-5(9H)-one A solution of 1.68 g (0.02 mole) of 3-amino-2H-1,2,4-triazole, 4.66 g (0.02 mole) of 1-phenyl-3-carbethoxy-4-pyrrolidone and 8 ml of n-butanol is refluxed for 6 hours. The reaction mixture is allowed to stand at room temperature for 16 hours. The precipitated crystals are filtered, washed with acetic acid, dried, dissolved in hot dimethyl formamide and precipitated by adding acetonitrile. Thus 2.64 g of the desired compound are obtained, yield 50%, m.p.: 262°–264° C.

EXAMPLE 14

7-Benzyl-2-methylthio-6,7,8,9-tetrahydro-pyrido[4,3-d]-1,2,4-triazolo[1,5-a]pyrimidine-5(10H)-one and 7-benzyl-2-methylthio-6,7,8,9-tetrahydro-pyrido[4,3-d]-1,2,4-triazolo[1,5-a]pyrimidine-6(10H)-one A solution of 39.05 g (0.3 mole) of 5-amino-3-methylthio-1H-1,2,4-triazole, 85.1 g (0.3 mole) of 1-benzyl-3-carbomethoxy-4-piperidone-hydrochloride and 125 ml of acetic acid is heated to boiling for 5.5 hours. The reaction mixture is cooled and 350 ml of concentrated ammonium hydroxide are added. The mixture is allowed to stand for 16 hours at room temperature, the precipitated crystals are filtered and washed with water. The product is heated to boiling in 300 ml of methanol for 15 minutes and filtered again. The product is dissolved in hot dimethyl formamide, precipitated by adding acetonitrile, filtered and washed with acetonitrile. Thus 53.6 g of 7-benzyl-2-methylthio-6,7,8,9-tetrahydro-pyrido[4,3-d]-1,2,4-triazolo[1,5-a]pyrimidine-5(10H)-one are obtained, yield 54%, m.p.: 245°–247° C.

The above-mentioned methanolic filtrate is cooled to room temperature. The precipitated crystals are filtered, washed with methanol, dissolved in hot dimethyl formamide, precipitated by adding acetonitrile, filtered and washed with acetonitrile. Thus 28.1 g of 7-benzyl-2-methylthio-6,7,8,9-tetrahydro-pyrido[4,3-d]-1,2,4-triazolo[1,5-a]pyrimidine-6(10H)-one are obtained, yield 29%, m.p.: 236°–238° C.

EXAMPLE 15

7-Benzyl-10-methyl-2-morpholino-6,7,8,9-tetrahydropyrido[4,3-d]-1,2,4-triazolo[1,5-a]pyrimidine-6(10H)-one In a flask equipped with a stirrer and closed by a calcium chloride tube 0.50 g (0.00135 mole) of 7-benzyl-2-morpholino-6,7,8,9-tetrahydro-pyrido[4,3-d]-1,2,4-triazolo[1,5-a]pyrimidine-6(10H)-one are suspended in 15 ml of dimethyl formamide, whereupon to the suspension 0.06 g (0.002 mole) of 80% sodium hydride are added under constant stirring. The mixture is heated to 40°–50° C. under continued stirring, then stirred at this temperature for a further period of 10 minutes and cooled to 0° C. Under stirring 0.36 g (0.0025 mole; 0.16 ml) of methyl iodide are added dropwise. The reaction mixture is stirred at 0° C. for half an hour and allowed to stand for 16 hours. The reaction mixture thus obtained is decomposed with 75 ml of water and extracted four times with 30 ml of chloroform each. The united chloroform phases are dried over sodium sulfate, filtered and evaporated to dryness in vacuo. The residue is recrystallized from isopropanol. Thus 0.34 g of the desired compound is obtained, yield 66%, m.p.: 182°–184° C.

EXAMPLE 16

7,10-Dibenzyl-2-morpholino-6,7,8,9-tetrahydropyrido[4,3-d]-1,2,4-triazolo[1,5-a]pyrimidine-5(10H)-one In a flask equipped with a stirrer and closed by a calcium chloride tube 2.07 g (0.0075 mole) of 2-morpholino-6,7,8,9-tetrahydro-pyrido[4,3-d]-1,2,4-triazolo[1,5-a]-pyrimidine-5(10H)-one are suspended in 15 ml of dimethyl formamide. Under stirring 0.675 g (0.0225 mole) of 80% sodium hydride are added, the mixture is heated at 60°–70° C. under further stirring and stirred at this temperature for a further period of 30 minutes. Heating is stopped, the reaction mixture is allowed to cool to 40° C. and at this temperature 2.85 g (0.025 mole; 2.59 ml) of benzyl chloride are added dropwise. The reaction mixture is stirred at room temperature for 5 hours, allowed to stand overnight, whereupon 75 ml of water are added. The mixture is extracted three times with 30 ml of chloroform each, the united chloroform phases are dried over magnesium sulfate, filtered and evaporated to dryness in vacuo. The residue is recrystallized from dimethyl formamide. Thus 0.81 g of the desired compound is obtaind, yield 24%, m.p.: 185°–187° C.

EXAMPLE 17

7-Benzyl-2-methylthio-10-(2-piperidinoethyl)-6,7,8,9-tetrahydro-pyrido[4,3-d]-1,2,4-triazolo[1,5-a]pyrimidine-6(10H)-one A suspension of 9.82 g (0.03 mole) of 7-benzyl-2-methylthio-6,7,8,9-tetrahydro-pyrido[4,3-d]-1,2,4-triazolo[1,5-a]pyrimidine-6(10H)-one, 1.05 g (0.035 mole) of 80% sodium hydride and 30 ml of dimethyl formamide is stirred at 70°–80° C. for 2 hours. The reaction mixture is cooled to room temperature and a 17.3% xylene solution of 64 g (0.045 mole) of 2-piperidino ethyl chloride is added dropwise. The reaction mixture is stirred at 90° C. for 10 hours and allowed to stand at room temperature for 16 hours. After addition of 50 ml of water and mixture is extracted four times with 50 ml of chloroform each. The united chloroform extracts are dried over sodium sulfate, filtered and evaporated to dryness in vacuo. The residue is recrystallized from 2-propanol. Thus 7.63 g of the desired compound are obtained, yield 58%, m.p.: 116°–119° C.

EXAMPLE 17a

7-Benzyl-2-methylthio-10-(2-piperidino-ethyl)-6,7,8,9-tetrahydro-pyrido[4,3-d]-1,2,4-triazolo[1,5-a]pyrimidine-5-(10H)-one One proceeds as described in Example 17, except that 7-benzyl-2-methylthio-6,7,8,9-tetrahydro-pyrido[4,3-d]-1,2,4-triazolo[1,5-a]pyrimidine-6(10H)-one is replaced by 7-benzyl-2-methylthio-6,7,8,9-tetrahydro-pyrido[4,3-d]-1,2,4-triazolo[1,5-a]pyrimidine-5(10H)-one. Yield 44%, m.p.: 108°–111° C.

EXAMPLE 17b

7-Benzyl-10-(3-dimethylaminopropyl)-2-methylthio-6,7,8,9-tetrahydro-pyrido[4,3-d]-1,2,4-triazolo[1,5-a]pyrimidine-6(10H)-one One proceeds as described in Example 17, except that the xylene solution of 2-piperidino ethyl chloride is replaced by a xylene solution of 3-(dimethylamino)-propyl chloride. Yield 37%, m.p.: 118°–120° C.

EXAMPLE 17c

7-Benzyl-10-(3-dimethylaminopropyl)-2-(2-methyl-piperazino)-6,7,8,9-tetrahydro-pyrido[4,3-d]-1,2,4-triazolo[1,5-a]pyrimidine-6(10H)-one One proceeds according to Example 17b, except that 7-benzyl-2-methylthio-6,7,8,9-tetrahydro-pyrido[4,3-d]-1,2,4-triazolo[1,5-a]pyrimidine-6-(10H)-one is replaced by 7-benzyl-2-(4-methyl-piperazino)-6,7,8,9-tetrahydropyrido[4,3-d]-1,2,4-triazolo[1,5-a]pyrimidine-6(10H)-one, yield 51%, m.p.: 110°–113° C.

EXAMPLE 17d

7-Benzyl-10-(3-dimethylamino-2-methyl-propyl)-2-morpholino-6,7,8,9-tetrahydro-pyrido[4,3-d]-1,2,4-triazolo[1,5-a]pyrimidine-6(10H)-one One proceeds according to Example 17, except that 7-benzyl-2-methylthio-6,7,8,9-tetrahydro-pyrido[4,3-d]-1,2,4-triazolo[1,5-a]pyrimidine-6(10H)-one is replaced by 7-benzyl-2-morpholino-6,7,8,9-tetrahydro-pyrido[4,3-d]-1,2,4-triazolo[1,5-a]pyrimidine-6(10H)-one and the xylene solution of 2-piperidino ethyl chloride is replaced by a xylene solution of 3-dimethylamino-2-methyl-propyl chloride. Yield 53%, m.p.: 143°–146° C.

EXAMPLE 18

7-Benzyl-2-morpholino-10-(2-piperidinoethyl)-6,7,8,9-tetrahydro-pyrido[4,3-d]-1,2,4-triazolo[1,5-a]pyrimidine-5(10H)-one One proceeds according to Example 17, except that 7-benzyl-2-methylthio-6,7,8,9-tetrahydro-pyrido[4,3-d]-1,2,4-triazolo[1,5-a]pyrimidine-6(10H)-one is replaced by 7-benzyl-2-morpholino-6,7,8,9-tetrahydro-pyrido[4,3-d]-1,2,4-triazolo[1,5-a]pyrimidine-5(10H)-one. Yield 37%, m.p.: 193°–195° C.

EXAMPLE 18a

7-Benzyl-10-(3-dimethylaminopropyl)-2-morpholino-6,7,8,9-tetrahydro-pyrido[4,3-d]-1,2,4-triazolo[1,5-a]pyrimidine-5(10H)-one One proceeds according to Example 18, except that the xylene solution of 2-piperidino ethyl chloride is replaced by a xylene solution of 3-dimethylamino propyl chloride. Yield 36%, m.p.: 85°–90° C.

EXAMPLE 18b

7-Benzyl-10-(2-dimethylamino-1-methyl-ethyl)-2-morpholino-6,7,8,9-tetrahydro-pyrido[4,3-d]-1,2,4-triazolo[1,5-a]pyrimidine-5(10H)-one One proceeds according to Example 18, except that the xylene solution of 2-piperidino-ethyl chloride is replaced by xylene solution of 2-dimethylamino-1-methyl-ethyl chloride. Yield 61%, m.p.: 163°–167° C.

EXAMPLE 18c

7-Benzyl-2-morpholino-10-(3-morpholinopropyl)-6,7,8,9-tetrahydro-pyrido[4,3-d]-1,2,4-triazolo[1,5-a]pyrimidine-5(10H)-one One proceeds according to Example 18, except that the xylene solution of 2-piperidino ethyl chloride is replaced by 3-morpholino propyl chloride. Yield 55%, m.p.: 128°–130° C.

EXAMPLE 18d

7-Benzyl-10-(3-dimethylamino-2-methyl-propyl)-2-morpholino-6,7,8,9-tetrahydro-pyrido[4,3-d]-1,2,4-triazolo[1,5-a]pyrimidine-5(10H)-one One proceeds according to Example 18, except that the xylene solution of 2-piperidino ethyl chloride is replaced by a xylene solution of 3-dimethylamino-2-methylpropyl chloride. Yield 43%, mp.: 121°–125° C.

EXAMPLE 18e

7-Benzyl-10-(3-dibenzylamino-propyl)-2-dimethylamino-6,7,8,9-tetrahydro-pyrido[4,3-d]-1,2,4-triazolo[1,5-a]pyrimidine-5(10H)-one One proceeds according to Example 18, except that 7-benzyl-2-morpholino-6,7,8,9-tetrahydro-pyrido[4,3-d]-1,2,4-triazolo[1,5-a]pyrimidine-5(10H)-one is replaced by 7-benzyl-2-dimethylamino-6,7,8,9-tetrahydro-pyrido[4,3-d]-1,2,4-triazolo[1,5-a]pyrimidine-5-(10H)-one and the xylene solution of 2-piperidino ethyl chloride is replaced by 3-dibenzylamino-propyl chloride. Yield 63%, m.p.: 139°–141° C.

EXAMPLE 19

8-Benzyl-10-(3-dimethylaminopropyl)-2-morpholino-6,7,8,9-tetrahydro-pyrido[3,4-d]-1,2,4-triazolo[1,5-a]pyrimidine-5(10H)-one To a suspension of 14.66 g (0.04 mole) of 8-benzyl-2-morpholino-6,7,8,9-tetrahydro-pyrido[3,4-d]-1,2,4-triazolo[1,5-a]pyrimidine-5(10H)-one and 30 ml of dimethyl formamide 1.50 g (0.05 mole) of 80% sodium hydride are added, whereupon the mixture is stirred at room temperature for 2 hours and at 60°–70° C. for an hour. The mixture is cooled to room temperature and a 41.5% toluene solution of 6.08 g (0.05 mole) of 3-dimethylaminopropyl chloride is added. The reaction mixture is stirred at 40° C. for 20 hours and filtered. To the product 100 ml of water are added and the mixture is extracted six times with 60 ml of chloroform each. The united chloroform extracts are dried over sodium sulfate, clarified with activated charcoal, filtered and evaporated to dryness in vacuo. The residue is recrystallized from 2-propanol. Thus 5.78 g of the desired compound are obtained, yield 32%, m.p.: 167°–169° C.

EXAMPLE 19a

8-Benzyl-10-(2-dimethylamino-1-methyl-ethyl)-2-morpholino-6,7,8,9-tetrahydro-pyrido[3,4-d]-1,2,4-triazolo[1,5-a]pyrimidine-5(10H)-one One proceeds according to Example 19, except that the toluene solution of 3-dimethylamino-propyl chloride is replaced by a xylene solution of 2-dimethylamino-1-methyl-ethyl-chloride. The reaction is carried out at 90° C., instead of 40° C. Yield 49%, m.p.: 168°–172° C.

EXAMPLE 19b

8-Benzyl-2-morpholino-10-(3-morpholinopropyl)-6,7,8,9-tetrahydro-pyrido[3,4-d]-1,2,4-triazolo[1,5-a]pyrimidine-5(10H)-one One proceeds according to Example 19, except that the toluene solution of 3-dimethylamino-propyl chloride is replaced by 3-morpholino-propylchloride and the reaction is carried out at 90° C., instead of 40° C. Yield 39%, m.p.: 155°–159° C.

EXAMPLE 19c

8-Benzyl-2-morpholino-10-(2-piperidino-ethyl)-6,7,8,9-tetrahydro-pyrido[3,4-d]-1,2,4-triazolo[1,5-a]pyrimidine-5(10H)-one One proceeds according to Example 19, except that the toluene solution of 3-dimethylamino-propyl chloride is replaced by xylene solution of 2-piperidino ethyl chloride. The reaction is carried out at 90° C., instead of 40° C. Yield 42%, m.p.: 172°–174° C.

EXAMPLE 19d

8-Benzyl-10-(3-dimethylamino-2-methyl-propyl)-2-morpholino-6,7,8,9-tetrahydro-pyrido[3,4-d]-1,2,4-triazolo[1,5-a]pyrimidine-5(10H)-one One proceeds according to Example 19, except that the toluene solution of 3-dimethylamino-propyl chloride is replaced by a xylene solution of 3-dimethylamino-2-methylpropyl chloride and the reaction is carried out at 90° C., instead of 40° C. Yield 65%, m.p.: 120°–123° C.

EXAMPLE 19e

8-Benzyl-10-(3-dimethylamino-2-methyl-propyl)-2-methylthio-6,7,8,9-tetrahydro-pyrido[3,4-d]-1,2,4-triazolo[1,5-a]pyrimidine-5(10H)-one One proceeds according to Example 19d, except that 8-benzyl-2-morpholino-6,7,8,9-tetrahydro-pyrido[3,4-d]-1,2,4-triazolo[1,5-a]pyrimidine-5(10H)-one is replaced by 8-benzyl-2-methylthio-6,7,8,9-tetrahydro-pyrido[3,4-d]-1,2,4-triazolo[1,5-a]pyrimidine-5(10H)-one. Yield 40%, m.p.: 132°–135° C.

EXAMPLE 19f

8-Benzyl-2-methylthio-10-(3-morpholinopropyl)-6,7,8,9-tetrahydro-pyrido[3,4-d]-1,2,4-triazolo[1,5-a]pyrimidine-5(10H)-one One proceeds according to Example 19b, except that 8-benzyl-2-morpholino-6,7,8,9-tetrahydro-pyrido[3,4-d]-1,2,4-triazolo[1,5-a]pyrimidine-5(10H)-one is replaced by 8-benzyl-2-methylthio-6,7,8,9-tetrahydro-pyrido[3,4-d]-1,2,4-triazolo[1,5-a]pyrimidine-5(10H)-one, yield 49%, m.p.: 154°–155° C.

EXAMPLE 19g

7-Benzyl-2-methylthio-10-(3-morpholino-propyl)-6,7,8,9-tetrahydro-pyrido[4,3-d]-1,2,4-triazolo[1,5-a]pyrimidine-5(10H)-one fumarate One proceeds according to Example 19f, except that 8-benzyl-2-methylthio-6,7,8,9-tetrahydro-pyrido[3,4-d]-1,2,4-triazolo[1,5-a]pyrimidine-5(10H)-one is replaced by 7-benzyl-2-methylthio-6,7,8,9-tetrahydro-pyrido[3,4-d]-1,2,4-triazolo[1,5-a]pyrimidine-5(10H)-one. The compound thus obtained is dissolved in hot 2-propanol and a molar equivalent aomount of fumaric acid is added. The crystallized fumarate is filtered. Yield 25%, m.p.: 179°–180° C.

EXAMPLE 20

8-Benzyl-2-morpholino-10-(2-pyrrolidinoethyl)-6,7,8,9-tetrahydro-pyrido[3,4-d]-1,2,4-triazolo[1,5-a]pyrimidine-5(10H)-one One proceeds according to Example 18, except that the toluene solution of 3-dimethylamino-propyl chloride is replaced by a xylene solution of 2-pyrrolidinoethyl chloride and the reaction is carried out at 70°–80° C., instead of 30°–40° C. Thus 7.60 g of the desired compound are obtained, yield 41%, m.p.: 184°–186° C.

EXAMPLE 21

7-acetyl-7-methylthio-6,7,8,9-tetrahydro-pyrido[4,3-d]-1,2,4-triazolo[1,5-a]pyrimidine-5(10H)-one To a mixture of 1.21 g (0.012 mole, 1.66 ml) of triethyl amine and 5 ml of dimethyl formamide 0.95 g (0.004 mole) of 2-methylthio-6,7,8,9-tetrahydro-[4,3-d]-1,2,4-triazolo[1,5-a]pyrimidine-5(10H)-one are added. To the reaction mixture 1.21 g (0.012 mole, 0.85 ml) of acetyl chloride are added dropwise under stirring. The reaction mixture is heated to boiling at 60°–65° C. for 16 hours under stirring, the cooled to room temperature. The precipitated crystals are filtered, washed with water and acetone. The solid is dissolved in 4 ml of hot dimethyl formamide and precipitated by adding 15 ml of acetontrile. Thus 0.54 g of the desired compound is obtained, yield 50%, m.p.: 284°–286° C.

EXAMPLE 22

7-Acetyl-2-morpholino-6,7,8,9-tetrahydro-pyrido[4,3-d]-1,2,4-triazolo[1,5-a]pyrimidine-5(10H)-one To a mixture of 0.50 g (0.005 mole, 0.69 ml) of triethyl amine and 4 ml of dimethyl formamide 0.83 g (0.003 mole) of 2-morpholino-6,7,8,9-tetrahidro-pyrido[4,3-d]-1,2,4-triazolo[1,5-a]pyrimidine-5(10H)-one are added. To the reaction mixture 0.39 g (0.005 mole; 0.35 ml) of acetyl chloride is added under stirring. The reaction mixture is stirred at 40°–50° C. for three hours and a half, whereupon it is allowed to stand at room temperature for 16 hours, and 25 ml of water are added. The precipitated crystals are filtered, washed with water, dissolved in 18 ml of hot dimethyl formamide and precipitated by adding 18 ml of acetonitrile. The precipitated product is filtered, washed with acetone and the above purification step is repeated. Thus 0.39 g of the desired compound is obtained, yield 59%, m.p.: 310°–313° C.

EXAMPLE 23

2-Morpholino-7-propionyl-6,7,8,9-tetrahydro-pyrido[4,3-d]-1,2,4-triazolo[1,5-a]pyrimidine-5(10H)-one To a mixture of 0.50 g (0.005 mole, 0.69 ml) of triethyl amine, 4 ml of dimethyl formamide, 1 ml of hexamethyl phosphoric triamide and 0.828 g (0.003 mole) of 2-morpholino-6,7,8,9-tetrahydro-pyrido[4,3-d]-1,2,4-triazolo[1,5-a]-pyrimidine-5(10H)-one are added. To the mixture 0.46 g (0.005 mole, 0.43 ml) of propionyl chloride are added under stirring and the reaction mixture is first stirred at 25° C. for six hours and a half and then allowed to stand at room temperature for 16 hours. After addition of 25 ml of water the precipitated crystals are filtered and washed with acetone. The solid is dissolved in 6 ml of hot dimethyl formamide and precipitated by adding 15 ml of acetonitrile. Thus 0.63 g of the desired compound is obtained, yield 63%, m.p.: 278°–280° C.

EXAMPLE 24

7-n-Butyl-thiocarbamoyl-2-morpholino-6,7,8,9-tetrahydro-pyrido[4,3-d]-1,2,4-triazolo-[1,5-a]pyrimidine-5(10H)-one A mixture of 1.11 g (0.004 mole) of 2-morpholino-6,7,8,9-tetrahydro-pyrido[4,3-d]-1,2,4-triazolo[1,5-a]pyrimidine-5(10H)-one, 0.46 g (0.004 mole) of n-butyl-isothiocyanate, 3 ml of dimethyl formamide and 1 ml of hexamethyl phophoric triamide is stirred at 130°–140° C. for 8 hours. The reaction mixture is allowed to stand at room temperature for 16 hours, whereupon 30 ml of water are added. The precipitated crystals are filtered, washed with water and acetone, dissolved in hot dimethyl formamide and precipitated by adding acetonitrile. Thus 1.03 g of the desired compound are obtained, yield 66%, m.p.: 243°–245° C.

In an analogous manner to the preceding Example the following compounds are prepared:

EXAMPLE 25

7-Allyl-thiocarbamoyl-2-morpholino-6,7,8,9-tetrahydropyrido[4,3-d]-1,2,4-triazolo[1,5-a]pyrimidine-5(10H)-one, m.p.: 237°–238° C., yield 57%.

EXAMPLE 26

7-Octadecyl-carbamoyl-2-morpholino-6,7,8,9-tetrahydro-pyrido[4,3-d]-1,2,4-triazolo[1,5-a]pyrimidine-5(10H)-one, m.p.: 228°–230° C., yield 58%.

EXAMPLE 27

7-Cyclohexyl-carbamoyl-2-morpholino-6,7,8,9-tetrahydro-pyrido[4,3-d]-1,2,4-triazolo[1,5-a]pyrimidine-5(10H)-one, m.p.: 258°–260° C., yield 50%.

EXAMPLE 28

7-Phenyl-carbamoyl-2-morpholino-6,7,8,9-tetrahydropyrido[4,3-d]-1,2,4-triazolo[1,5-a]pyrimidine-5(10H)-one, m.p.: 278°–281° C., yield 85%.

EXAMPLE 29

7-Phenyl-thiocarbamoyl-2-morpholino-6,7,8,9-tetrahydro-pyrido[4,3-d]-1,2,4-triazolo[1,5-a]pyrimidine-5(10H)-one, m.p.: 251°–252∞ C., yield 86%.

EXAMPLE 30

7-(3-Trifluoromethyl)-carbamoyl-2-morpholino-6,7,8,9-tetrahydro-pyrido[4,3-d]-1,2,4-triazolo[1,5-a]-pyrimidine-5(10H)-one, m.p.: 266°–268° C., yield 25%.

EXAMPLE 31

7-Benzoyl-carbamoyl-2-morpholino-6,7,8,9-tetrahydro-pyrido[4,3-d]-1,2,4-triazolo[1,5-a]pyrimidine-5(10H)-one, m.p.: 305°–307° C., yield 61%.

EXAMPLE 32

7-Benzyl-thiocarbamoyl-2-morpholino-6,7,8,9-tetrahydro-pyrido[4,3-d]-1,2,4-triazolo[1,5-a]pyrimidine-5(10H)-one, m.p.: 256°–259° C., yield 79%.

EXAMPLE 33

7-(2,6-Dimethyl-phenyl)-thiocarbamoyl-2-morpholino-6,7,8,9-tetrahydro-pyrido[4,3-d]-1,2,4-triazolo[1,5-a]pyrimidine-5(10H)-one, yield 74%, m.p.: 247°–248° C.

What we claim is:

1. Condensed cyclic triazole derivatives of the general Formula I

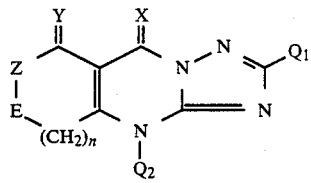

(wherein
Q$_1$ is hydrogen or a group of the general Formula —NR$_3$R$_4$ wherein
R$_3$ and R$_4$ each stand for hydrogen or straight or branched chain, saturated or unsaturated lower alkyl, aralkyl or aryl, optionally substituted by one or more lower alkyl and/or halogen; or R$_3$ and R$_4$ together with the adjacent nitrogen atom, they are attached to, form a 5–8 membered heterocyclic ring;
—SR$_6$ wherein
R$_6$ stands for lower alkyl or aralkyl being unsubstituted or substituted by one or more halogen atom(s);
Q$_2$ stands for hydrogen, lower alkyl, aralkyl or a group of the general formula

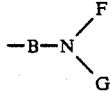

wherein

B is lower alkylene;

F and G each stand for lower alkyl or aralkyl or together with the adjacent nitrogen atom, they are attached to, form a 5-8 membered heterocyclic ring;

n is 0 or 1;

X and Y stand for =O or =H$_2$, with the proviso that X and Y are different;

E and Z stand for —CH$_2$—, —NH—, —N—alkyl—, —N—aralkyl—, or

NCOR$_1$ wherein
R$_1$ is lower alkyl or aralkyl; or

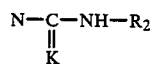

wherein

K is =O or =S and

R$_2$ stands for straight or branched chain alkyl, aralkyl, or aryl which can be either unsubstituted or can bear one or more haloalkyl and/or alkyl substituent(s);

with the proviso that Z and E are different and one of Z and E represents —CH$_2$—) and mixtures and pharmaceutically acceptable salts thereof.

2. Pharmaceutical compositions comprising as active ingredient at least one compound of the general Formula I (wherein Q$_1$, Q$_2$, Z, E, , Y and n are as stated in claim 1) or a pharmaceutically acceptable salt thereof with suitable inert solid or liquid carriers.

3. A method for sedating and tranquillizing a patient in need thereof which comprises administering to said patient an effective amount of a pharmaceutical composition as defined in claim 2.

* * * * *

UNITED STATES PATENT AND TRADEMARK OFFICE
CERTIFICATE OF CORRECTION

PATENT NO. : 4,831,029
DATED : May 16, 1989
INVENTOR(S) : Reiter et al.

It is certified that error appears in the above-identified patent and that said Letters Patent is hereby corrected as shown below:

IN THE CLAIMS

Claim 2, Line 3

"(Wherein $Q_1$, $Q_2$, Z, E,,Y and n are as stated in claim 1)"

Should read

"(Wherein $Q_1$, $Q_2$, Z, E, X, Y and n are as stated in claim 1)"

Signed and Sealed this

Tenth Day of October, 1989

*Attest:*

DONALD J. QUIGG

*Attesting Officer*     *Commissioner of Patents and Trademarks*